(12) United States Patent
Giesen et al.

(10) Patent No.: US 8,802,386 B2
(45) Date of Patent: Aug. 12, 2014

(54) DIAGNOSTIC TEST FOR DETERMINING THE CONCENTRATION OF TRANSIENT PROTEOLYTIC ACTIVITY IN COMPOSITE BIOLOGICAL MEDIA

(75) Inventors: Peter Giesen, Maastricht (NL); Hendrik Hemker, Maastricht (NL); Raed Al Dieri, Maastricht (NL); Suzette L. Beguin, Villers-Agron-Aiguizy (FR); Robert Wagenvoord, Maastricht (NL)

(73) Assignee: Synapse B.V., Maastricht (NL)

( * ) Notice: Subject to any disclaimer, the term of this patent is extended or adjusted under 35 U.S.C. 154(b) by 1218 days.

(21) Appl. No.: 10/514,269

(22) PCT Filed: May 1, 2003

(86) PCT No.: PCT/EP03/04705
§ 371 (c)(1),
(2), (4) Date: Aug. 1, 2005

(87) PCT Pub. No.: WO03/093831
PCT Pub. Date: Nov. 13, 2003

(65) Prior Publication Data
US 2006/0051828 A1    Mar. 9, 2006

(30) Foreign Application Priority Data
May 1, 2002 (EP) ..................................... 02076744

(51) Int. Cl.
*C12Q 1/56* (2006.01)
(52) U.S. Cl.
USPC ............. 435/13; 435/212; 435/214; 424/1.69
(58) Field of Classification Search
USPC ........................................................ 435/13
See application file for complete search history.

(56) References Cited

U.S. PATENT DOCUMENTS 6,740,496 B1 * 5/2004 Hemker et al. ................. 435/13

FOREIGN PATENT DOCUMENTS

WO    WO 00/52199    *  9/2000 ............... C12Q 1/56

OTHER PUBLICATIONS

Hemker et al , "The thrombogram:Monitoring thrombin generetion in platelet rich plasma"Thromb. Haemost. 2000,p. 589-91.*
Wielders et al, "The routine determination of the endogeneous thrombin potential, firstresults in different forms of hyperohypocoagulability,"Thromb Haemmost.,1997 p. 629-36.*
Raus et al., Comparison of the affinities to bovine and human prothrombin of the Staphylocoagulases from *Staphylococcus intermedius* and *Staphylococcus aureus* of Animal Origin, Journal of CLinical Microbiology, Mar. 1991, p. 570-572.*
Lewis et al., Catalytic competence of human alpha- and gamma-thrombin in the activation of fibrinogen and Factor XIII, abstract, Biochemistry, 1987.*

* cited by examiner

*Primary Examiner* — Jon P Weber
*Assistant Examiner* — Tiffany Gough
(74) *Attorney, Agent, or Firm* — William D. Schmidt, Esq.; Sorell, Lenna & Schmidt LLP

(57) ABSTRACT

A method is provided for determining in real time the course of thrombin activity in a sample of blood or plasma as it appears in and disappears from the simple which comprises adding a thrombin substrate to the sample that, per unit time, produces a detectable signal in a quantity that bears relation to the amount of thrombin present. Simultaneously, in a control sample of the same blood or plasma in which thrombin generation is not triggered, the activity of a standard preparation with invariable thrombin activity is measured. The exact molar amount of thrombin present at any moment is obtained by comparison of the activity measured in clotting blood and the simultaneously measured calibrator. The method is useful inter alia for diagnosing hyper- and hypo-coaguable states, either congenital, acquired or drug-induced in humans and animals. Also provided is a kit for use in this method.

13 Claims, 9 Drawing Sheets

DIAGNOSTIC TEST FOR DETERMINING THE CONCENTRATION OF TRANSIENT PROTEOLYTIC ACTIVITY IN COMPOSITE BIOLOGICAL MEDIA

FIELD OF THE INVENTION

The present invention is in the field of diagnostics and relates more particularly to a method of determining, in real time, the course of the concentration of biologically active enzymes that are transiently present in blood or other body fluids, and to a test kit for carrying out this method.

BACKGROUND OF THE INVENTION a. Introduction

The generation and decay of proteolytic enzymes in body fluids is a key element in processes as diverse as digestion, inflammation, blood coagulation and thrombosis. To give an example: Thrombin is an enzyme that is transiently present in clotting blood and that is the key enzyme of haemostasis and thrombosis. Disorders of the haemostatic thrombotic system (HTS) are pivotal in over half of all invalidating and lethal disease. Quantitatively the less important ones, haemophilia and lung embolism, come readily to mind. It is not so widely acknowledged that arterial thrombosis causes coronary infarction or that one out of ten of the elderly risk loss of brain function through clots obstructing brain arteries (embolisation on the basis of atrial fibrillation and carotid emboli), or that seriously ill patients may bleed to death because of disorders of the clotting system (victims of accidents and patients suffering from sepsis with fatal intravascular coagulation). It is insufficiently recognised that more people die from arterial thrombosis than from malignancies and more from venous thrombosis than from accidents. In view of such medical importance it is surprising to note that there is no valid function test of the HTS available to the clinician today.

In body fluids there exist several more physiologically important biochemical systems that act through activation and subsequent inactivation of proteolytic enzymes, such as, in blood, the coagulation system, the fibrinolytic system and the complement system, and in gastrointestinal juices the digestive enzymes. For the assessment of biological function of these systems it is important to be able to follow the course of such proteolytic activity as it develops after triggering in a sample of the body fluid ex vivo in time. Such function assessment is of paramount diagnostic importance because disturbances of such systems can lead to fatal diseases like coronary infarction, stroke or fatal bleeding (blood coagulation and fibrinolysis), generalised infections and autoimmune diseases (complement system) or disturbed absorption of food (gastrointestinal juices).

In haemostasis and thrombosis, clotting times are the best assessments available today and they are insensitive to mild haemostatic disorders (e.g. carriers of haemophilia, mild liver disease) or to increased coagulability that leads to increased thrombosis risk. Clotting tests often need to be adapted to a specific use. For example, the thromboplastin time (=Prothrombin time (PT), =Quick time) can be used for diagnosis of serious liver disease or treatment with anticoagulants but is not prolonged by haemophilia or heparin treatment. Much of the art and science of the clinical coagulation lab resides in knowing how to interpret the scattered information that can be obtained from clotting times of different types, platelet aggregation, bleeding time etc.

The insufficiency of the over-all tests is partly compensated by a great variety of sophisticated tests of single components of the clotting system, so many indeed that a judicious selection should be made in every special case, which is the other half of the specific knowledge of the clinical haemostasis lab.

b. Mechanism of Thrombin Generation

The mechanism of thrombin generation in blood plasma can be exemplified as follows. Tissue Factor (TF) is abundantly—but not exclusively—present in the vessel wall. When a blood vessel is damaged, the blood enters the tissues and the plasma protein factor VIIa (VIIa) can interact with TF. This triggers an extremely complicated set of interactions, between plasma proteins and blood platelets, which results in a transient burst of thrombin that remains limited in time and space, so that normally a wound stops bleeding but clotting is not propagated in the remainder of the body.

This mechanism can be shown to be so intricate, replete with positive and negative feedback reactions, that its action cannot be predicted from knowledge of its parts (irreducible complexity). Therefore, if one wants to assess the function of the haemostatic system the thrombin generation has to be investigated as it occurs in the body, or in an isolated part of the body, i.e. a sample of blood or platelet-rich plasma The interaction between blood platelets and plasma factor is of particular importance, the information to be obtained from platelet-poor plasma being essentially deficient. See, e.g., Béguin S., R. Kumar, I. Keularts, U. Seligsohn, B. C. Coller and H. C. Hemker, *Fibrin-Dependent Platelet Procoagulant Activity Requires GPIb Receptors and Von Willebrand Factor*, Blood (1999) 93:564-570; Béguin, S. and R. Kumar, supra (1997)].

An important fraction (≈30%) of all thrombin formed in clotting plasma is bound to the fibrin clot. Clot-bound thrombin does retain its thrombotic properties, it can clot fibrinogen, activate factors V, VIII and XI as well as platelets [Béguin, S. and R. Kumar, Thromb. Haemost. (1997) 78:590-594; Kumar, R., S. Béguin, and H. C. Hemker, Thromb. Haemost. (1994) 72:713-721, and (1995) 74:962-968]. It is only partly inhibited by antithrombin. Therefore, it is essential that fibrin is present when investigating the function of the coagulation system.

In order to assess the function of such a system for diagnostic purposes and for the safe use of antithrombotic drugs a variety of tests has been developed of single components of the clotting system, which will be further detailed below.

As stated before, the thrombin activity that generates at the site of a lesion is an important determinant of the extent of the haemostatic-thrombotic reaction that ensues. Most of the thrombin (>95%) generates after the moment of clotting, therefore the clotting time is not automatically a good indicator of thrombin activity. Thrombin activity in clotting blood is a transient phenomenon and therefore should be measured during the clotting process.

A typical course of thrombin formation in clotting blood or plasma, also designated as the thrombin generation curve, is shown in FIG. 1. After a period in which no observable thrombin is formed, the concentration steeply goes up, rises to a peak and then goes down again. The parameters are the lag time, the area under the curve (AUC), also designated as the endogenous thrombin potential (ETP; see below), the peak height, and the time it takes to reach the peak.

c. Related Prior Art

A thrombin generation curve as shown in FIG. 1 is classically obtained via determination of the thrombin content in small subsamples taken at short intervals from clotting blood or plasma. See, e.g., R. Biggs and R. G. Macfarlane, *Human Blood Coagulation and its Disorders*, Blackwell Scientific Publications, Oxford 1953; W. Seegers, *Prothombin*, Harvard University Press, Cambridge Mass. 1962. This method generally requires separate analysis of the subsamples and allows the determination of only 3-5 curves simultaneously by the continuous occupation of a skilled laboratory worker. It is so labor intensive as to preclude its application in clinical or pharmaceutical routine.

EP-A-0 420 332 (equivalent to U.S. Pat. No. 5,192,689) discloses a method to determine the amount of thrombin which has been present in a sample of either clotting blood or plasma by measuring the amount of product that is produced from an artificial substrate during coagulation. This amount is proportional to the area under the thrombin generation curve, designated as the endogenous thrombin potential, ETP. The method comprises adding a thrombin formation activator to a sample of either clotting blood or plasma together with a thrombin substrate, wherein the amount and also the kinetic properties of the thrombin substrate are chosen such that the amount of thrombin generated in the sample cannot completely consume said thrombin substrate, thereby to produce a conversion product, measuring the amount of said conversion product thus produced, and from this determining the endogenous thrombin potential in the sample. This ETP-method can be illustrated by the following reactions:

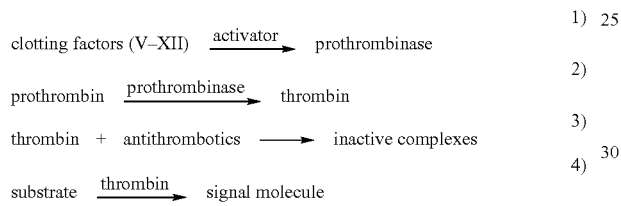

All reactions irreversible and therefore thrombin is only temporarily present in the reaction mixture. While thrombin is present, it participates in reaction 4, with the result that the degree of conversion of the substrate indicates the time for which, and the time to which, thrombin has catalyzed this reaction.

It is essential that the amount of substrate should not be exhausted before the thrombin disappears. For the amount of substrate converted to be an exact representation of the total amount of thrombin activity that developed, the reaction rate should be proportional to the concentration of thrombin at any instant in time. The essence of this ETP method is that the thrombin potential is determined as an end-point method without determination of the thrombin/time curve as such. In case the substrate would be short-measured, the end-point would be simply the maximum amount of product formed, and such figure has no meaning anyway.

Furthermore, the ETP-method is conducted in actual practice with a chromogenic substrate i.e. substrates with a chromophoric leaving group that is detected via optical density measurement. Fibrinogen, and consequently blood platelets, have to be removed from plasma because turbidity arising from the fibrinogen-fibrin conversion by thrombin makes further measurement impossible. Fibrinogen and platelets, however, are essential components of the clotting system that influence the course of thrombin formation. This puts a serious limit on the applicability of optical density as a detection method. Thus, assessment of the ETP in plasma containing platelets and/or fibrinogen would not be possible.

Continuous monitoring of thrombin concentration has been attempted through adding a suitable thrombin substrate to the clotting sample and monitoring the time course of appearance of the amidolytic split product. For example, a chromogenic substrate is used and the optical density is measured so as to monitor the development of p-nitro-aniline (Hemker H C, S. Wielders, H. Kessels, S. Béguin: Thromb Haemost. (1993) 70(4):617-24; Hemker H C, and S. Béguin: Thromb Haemost. (1995) 74(1):134-8). If the reaction velocity in such a test would be dependent upon thrombin concentration only and if the signal would be proportional to the amount of product, then the slope of the product curve would be proportional to the amount of thrombin present, so that the thrombin generation curve can be obtained from the first derivative of the product curve if the proportionality constant (Kc) is known.

In practice, however, the reaction velocity is not dependent upon the thrombin concentration only, the signal is not necessarily proportional to the amount of product and Kc is unknown. The reasons are the following:

A: Substrate consumption: The signal is not only dependent upon the activity of thrombin in the sample but also on the amount of substrate which, through the very enzyme activity itself, decreases in time. The effect can be attenuated by adding an excess of substrate but to a certain limit only. The substrate binds, reversibly, to the active centre of thrombin and thereby protects thrombin from inactivation by natural antithrombins. Abolishing the effect of substrate consumption to an acceptable degree is paid for by prolonging the experiment to last for about two hours. (The more substrate is added the more enzyme molecules are occupied and unavailable to the natural inactivation processes. This prolongs the duration of the experiment. At 1×Km the experiment is finished in 30 min, at 5 Km practical independence of substrate consumption is obtained but the experiment lasts 90 min). Also, at such concentrations of substrate, thrombin inhibition interferes with feedback reactions and it is no longer guaranteed that the natural process is measured. This is also the reason that, in a method meant to assess the area under the curve from the total amount of substrate converted, an excess of substrate has to be added such that extra antithrombin needs to be added in order to make the experiment practically possible (see EP-A-0 420 332, discussed above).

B: Changes in optical density occur through clotting of the plasma sample. The use of chromogenic substrates implies the removal of fibrinogen, and consequently blood platelets, that causes spurious increase of OD through scattering of light at the moment of clotting. Fibrinogen and platelets, however, are essential components of the clotting system that influence the course of thrombin formation (see above). This puts a serious limit on the applicability of optical density as a detection method. This problem can be circumvented by using a substrate that yields a fluorescent product [H. C. Hemker et al. *The thrombogram: monitoring thrombin generation in platelet rich plasma*. Thromb Haemost. 83:589-91 (2000)]. This, however, introduces the next problem:

C: In fluorescence measurements the signal is not linearly related to the amount of product. Notably the fluorescent signal is not linearly dependent upon the concentration of fluorescent product because fluorescent molecules absorb the light from other product molecules, the so called "inner filter effect". With fluorescent products, increasing substrate concentrations to several times Km, as required for limiting the effect of substrate consumption automatically also increases the inner filter effect.

Problem A is common to all continuous methods. Problem B can be circumvented by using a fluorogenic substrate but this introduces problem C.

D: Even if the problems A, B and C would not exist, the question remains of relating reaction velocity to thrombin concentration, i.e. determining the calibration constant Kc. This relation varies from experimental setup to experimental setup (e.g. is different in different fluorometers) and from sample to sample (e.g. due to color variations of the plasma). Addition of a known standard amount of thrombin to the sample is impossible because the enzyme added will disturb the physiological reactions. It is also impossible to add thrombin to a parallel non-clotting sample because it will be inactivated in the plasma.

The present invention aims at obviating these drawbacks by providing a method relating to the determination of thrombin in a blood or plasma sample which is essentially different from the ETP-method outlined above, in that no end-point determination of the amount of product is made but rather the course of the thrombin concentration curve in real time is determined and provided as a continuous signal, thereby giving more valuable and accurate information regarding such parameters as lag time and peak height. The latter is more important for measuring subtle differences in the activity of the clotting mechanism as will be further outlined below. In other words, the new method does not provide a single value of the amount of thrombin that had been present in a sample as in the ETP-method, but rather provides the course of the thrombin concentration in real time that is transiently present in the sample.

SUMMARY OF THE INVENTION

It has now surprisingly been found that the drawbacks outlined above can be conveniently obviated by measuring the concentration of thrombin in clotting plasma, with or without platelets, by monitoring the splitting of a suitable signal substrate and comparing it to a constant known thrombin activity in a parallel sample.

Therefore, in accordance with one aspect of the present invention a method is provided for determining in real time the course of proteolytic activity, said proteolytic activity being substantially thrombin activity, in a first biological sample as it appears in and disappears from the sample, which comprises the following steps:

a) adding a protease activator to said first sample to generate proteolytic activity;

b) adding a signal substrate to step a), said signal substrate causing a detectable signal related to the amount of conversion product formed upon reaction by the generated proteolytic activity, c) adding a means with a constant known stable proteolytic activity on the signal substrate as defined in step b) but otherwise inert, to a second parallel sample in which no proteolytic activity is triggered, wherein the means with a constant known stable proteolytic activity is selected from the group consisting of $\alpha_2$-macroglobulin-thrombin complex, staphylocoagulase-prothrombin complex, and gamma thrombin.

d) adding the same signal substrate as defined in step b) to step c), said signal substrate causing a detectable signal upon reaction by the means with known stable proteolytic activity, e) determining the time course of signal development in said first sample and said second parallel sample to provide a curve from each of them, f) comparing said curves to derive the course of proteolytic activity in time in the first sample.

In a preferred embodiment of the present invention a method is provided for determining in real time the course of proteolytic activity, said proteolytic activity being substantially thrombin activity in a first sample of blood or plasma as it appears in and disappears from the sample, which comprises the following steps:

a) adding a thrombin formation activator to said first sample to form thrombin;

b) adding a signal substrate to step a), said signal substrate causing a detectable signal related to the amount of conversion product formed upon reaction by the thrombin formed, c) adding a means with a constant known stable thrombin activity on the signal substrate as defined in step b) but otherwise inert, to a second parallel sample in which no thrombin activity is triggered, d) adding the same signal substrate as defined in step b) to step c), said signal substrate causing a detectable signal upon reaction by the means with known stable thrombin activity, e) determining the time course of signal development in said first sample and said second parallel sample to provide a curve from each of them, f) comparing said curves to derive the course of thrombin activity in time in the first sample.

The first biological sample is usually selected from blood, plasma which includes platelet-rich, platelet-poor or platelet-free plasma, saliva, serum, urine, cerebro-spinal fluid, sperm, and faces.

When carrying out the method of the invention on blood samples, blood is usually collected in tubes that contain either sodium citrate or EDTA, or the like, so that free calcium ions in the blood are bound and thrombin formation and clotting is prevented. Hence, in order to start thrombin generation, calcium should be added shortly before the start of the measurement. However, in case blood is not collected in sodium citrate, or the like, this addition of calcium may not be necessary. For instance when the method is used in a way that makes it possible to start the experiment within minutes after blood taking.

The proteolytic activity to be determined is usually selected from the group of activated clotting factor activity, including thrombin, activated fibrinolytic factor activity, and activated component of the complement system activity. The determination of the course of thrombin activity, in real time, from a sample of blood or plasma according to the method of the present invention is a preferred embodiment.

The signal substrate which is used in the present method is preferably selected from the group of compounds comprising a leaving group, said leaving group giving a detectable conversion product upon reaction by the proteolytic enzyme formed. This conversion product is usually determined by spectroscopy, in particular fluorescence (preferred), optical density, and NMR. Accordingly, said leaving group normally is a fluorescent group, a chromophoric group, a group releasing hydrogen ions, or the like. A suitable and preferred signal substrate for carrying out the method of the present invention is Z-Gly-Gly-Arg-AMC. In addition, suitable detectable conversion products include p-nitroanilide and 7-amino-4-methyl-coumarin.

Suitable means with a constant known stable proteolytic activity for carrying out the method of the present invention, as defined above, include $\alpha_2$-macroglobulin-thrombin complex (preferred), staphylocoagulase-prothrombin complex, and gamma thrombin. In addition, any proteolytic enzyme can be used which is modified in its secondary recognition sites in that its active center remains intact but its functional interaction with proteins in the reaction mixture is abolished.

Useful protease activators for carrying out the present method include calcium ions, phospholipids, Tissue Factor, soluble Tissue factor, thromboplastin, kaolin, and elagic acid.

According to another aspect of the present invention said first biological sample further comprises a pharmaceutical agent to be tested for its influence on the proteolytic system under study, such as the haemostatic-thrombotic system. Suitable pharmaceutical agents which can be tested in the present method are antithrombotic agents, such as anti-platelet agents and anticoagulating agents, for example heparin, dermatan sulphate, a direct thrombin-inhibitor, for example hirudin, argatroban or melagatran, and a factor Xa inhibitor, for example tick anticoagulant protein.

According to yet another aspect of the invention a kit is provided for carrying out the method for determining in real time the course of proteolytic activity, in particular thrombin activity, as defined above. Such a kit conveniently comprises one or more of the following components in suitable containers or other conventional packaging means:

a known concentration of $\alpha_2$M-thrombin complex
a PRP reagent for platelet-rich plasma to start the clotting reaction.
a PPP reagent for platelet-poor or platelet-free plasma to start the clotting reaction.
an additive facilitating diagnosis of the course of thrombin activity, in particular when specific abnormalities of the hemostatic-thrombotic system are encountered or expected. Suitable additives are, for example, thrombomodulin or activated protein C, which are useful inter alia for the diagnosis of factor V Leiden, or specific antithrombotic or antiplatelet drugs.
a reagent containing a signal substrate.
a software program directly loadable into the memory of a computer for calculating the thrombin activity curve as determined by the method as defined above, when said program is run on a computer.
an instruction manual.

The kit may suitably comprise freeze-dried reagents.

These and other objects of the present invention will be explained below in more detail.

DEFINITIONS

Figure 1:
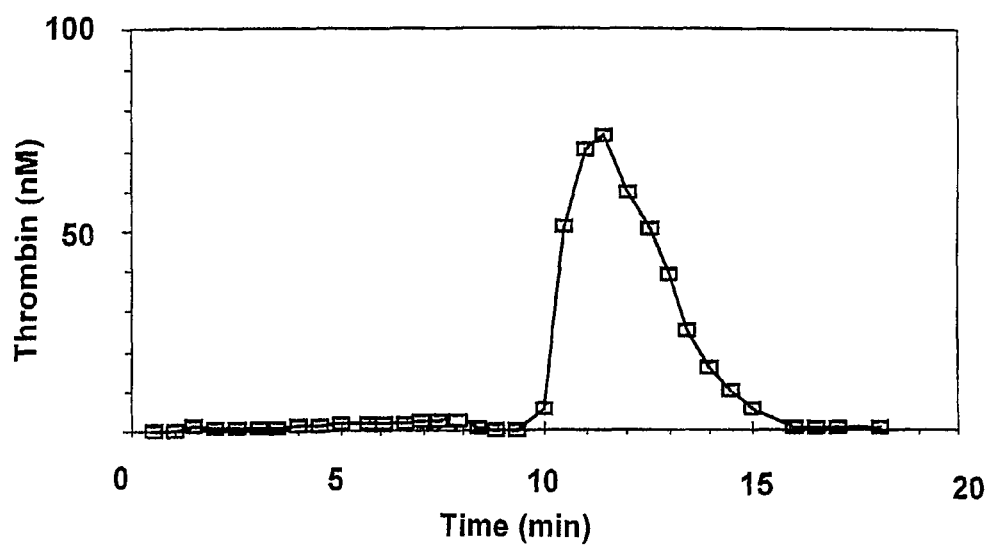
FIG. 1 is a thrombin generation curve showing a typical course of thrombin formation in clotting blood or plasma, determined by sub-sampling.

The term "transiently active" as used herein in connection with proteolytic enzymes occurring in a blood or plasma sample refers to the fact that the enzymatic activity, once the physiological process is started with the means known to the art, first arises and then subsides again to (near) zero activity in the end.

The term "composite biological media" as used herein refers to plasma, plasma with blood cells or whole blood or any other fluid of bodily origin or other, in which the biological process of enzyme activation and inactivation takes place.

The term "real time" as used herein is meant to indicate that the course of enzyme concentration in the medium is displayed simultaneously with the biological activation and inactivation of the sample is going on in the reaction vessel.

The term "lag time" as used herein is meant to indicate the time it takes before thrombin formation really starts.

As used herein, the term "peak height" means the maximal thrombin activity attained.

The term "steepness of ascending slope", as used herein, means the velocity of increase of thrombin concentration before the peak is reached.

The term "time to peak", as used herein, means the time between the start of the reaction and the moment that the peak is reached.

The term "ETP", as used herein, means the time integral of the curve until the moment of (near)zero thrombin activity is attained.

As used herein, the term "signal substrate" means a substrate that is cleaved by proteolytic enzyme(s) present in the medium, from which a leaving group is split off which is detectable by optical, NMR or other methods. Leaving groups which are optical detectable are, for example, p-nitroanilide and 7-amido-4-methyl-coumarin. p-Nitroanilide absorbs at 405 nm and 7-amido-4-methyl-coumarin is fluorescent (excitation at 390 nm and emission at 460 nm). Examples of NMR-active leaving groups are those containing $^{31}$P, $^{13}$C, or any other atom which can be detected with NMR or a similar technique. Also H$^+$ ions can be used as leaving group, which can be detected by measuring changes in the pH.

DETAILED DESCRIPTION OF THE INVENTION

In the following a typical description of the haemostatic and thrombotic system (HTS) will be given for the practice of the present invention with an emphasis on its most important enzyme, thrombin. It is to be noted, however, that the present invention also relates to other enzymes and to other physiological systems, such as other activated proteolytic enzymes (factors) of the clotting system in blood and plasma, plasmin and other activated components of the fibrinolytic system in blood and plasma, activated complement factors in blood and plasma, pepsin in gastric juice, trypsin and chymotrypsin in duodenic juice, and the like.

As mentioned above, in general transient enzymatic activities can be measured by adding a substrate that, upon conversion, produces a signal. Using a fluorogenic substrate in the present field such a method would typically comprise the addition of a fluorogenic substrate to blood (or another biological sample) in which thrombin generation has been triggered (using a method known in the art). Upon cleavage of the substrate a fluorescent product would be formed that is measurable at the appropriate wavelengths of excitation and emission.

Usually, in similar cases this can be arrived at by adding, to a second completely comparable sample, a fixed amount of the same substrate enzyme of known activity, also designated herein as a "calibrator", and comparing the known activity, in real time, to the activity of the sample investigated. However, in the present case because of its instability in and subsequent disappearance from plasma it is not possible to use thrombin itself as a calibrator. Also, immediately after addition of thrombin, clot formation will ensue which prevents proper mixing of reagents and induces erratic results.

Apart from the above-mentioned problems the units on the Y-axis would remain arbitrary, however, and vary with the progress of the experiment since the increase of the concentration of conversion product, through the so-called inner filter effect, together with the concomitant decrease of the available substrate would modify the relationship between thrombin concentration and velocity of signal production. In addition, the experiments are to be carried out in blood or plasma that, donor-dependently, would influence the signal through absorption of light and quenching of fluorescence.

Therefore each sample from each donor should be measured in such a way that the arbitrary units on the Y-axis can be attributed, in real time, to a valid amount of thrombin activity, expressed as a thrombin concentration in molar units.

The present invention is based upon the surprising finding that certain substances exhibit a constant thrombin-like activity which can be suitably used to assign absolute values (nM) to the first derivatives of the signals obtained from molecules that are split by thrombin as it develops in and disappears from clotting plasma. A suitable and particularly preferred substance is the irreversible complex of $\alpha_2$-macroglobulin (also designated herein as $\alpha_2$-M or $\alpha_2$M) and thrombin or, alternatively, the complex of staphylocoagulase and prothrombin.

If thrombin activity is monitored in a sample via e.g. its amidolytic action producing a fluorescent molecule the signal obtained cannot be directly related to the thrombin activity present for various reasons. The relationship between amount of fluorescent product formed per unit time and the increase of the fluorescent signal is dependent upon the instrument, upon the light-absorptive properties of the sample and upon the amount of product already present in the sample (the so-called inner-filter effect). The relationship between the amount of thrombin and the amount of fluorescent product is dependent upon the amount of substrate already consumed. Even though there is a direct relationship between product formation in time (dP/dt) and thrombin activity, it is instrument- and sample-dependent and will change during the experiment.

It is the very property of the coagulation system that thrombin appears and disappears after triggering of the system. Pathological changes in appearance and in disappearance rates cause serious illness. Therefore, the disappearance rate of thrombin in a sample is an important biological variable that must be left intact in the sample to be investigated. This same property makes it impossible to obtain a thrombin preparation with constant activity in the plasma that can be used as a calibrator to assign an absolute value to the thrombin activity.

It is an essential element of the present invention that the instrument, sample and time-dependency is cancelled out by the comparison of the signal from the clotting plasma to a means with constant thrombin-like activity. It was found that the $\alpha_2$-macroglobulin-thrombin complex has the desired characteristics to be such an excellent means providing a constant thrombin-like activity which can be easily determined by a person skilled in the art. Binding of thrombin to $\alpha_2$-macroglobulin renders thrombin immune to the natural inactivators present in plasma but leaves intact its capacity to split small substrates that upon cleavage release a molecule with light absorptive-, fluorescent-, or other signal-bearing properties. Because $\alpha_2$-macroglobulin is capable to bind a large variety of proteolytic enzymes it can also be used to prepare calibrators for other proteolytic enzymes (e.g. activated clotting factor X, plasmin, trypsis, pepsin, complement factor 3). As mentioned above, the complex of staphylocoagulase and prothrombin was found to possess similar characteristics in that it can also provide a constant thrombin-like activity that is not sensitive to plasmatic inhibitors, and can therefore be applied as an alternative calibrator system for other proteolytic enzymes.

The method according to the invention comprises splitting a sample of blood or plasma in two parts, or simply using two substantially identical samples, adding to both parts a substrate that, per unit time, produces a detectable signal in a quantity that bears relation to the thrombin activity present. In one sample thrombin generation (i.e. coagulation) is triggered by a method known in the art. To the other sample a preparation with independently determined and invariable thrombin activity, preferably the $\alpha_2$-macroglobulin-thrombin complex, as mentioned above, is added. Product formation is measured in the two samples preferably at the same time. The exact molar amount of thrombin present at any moment in the coagulating sample is obtained by comparison of the signal from that sample to the simultaneously measured signal from the sample to which the preparation with known and invariable thrombin activity has been added but in which thrombin formation has not been triggered.

In addition to the $\alpha_2$-macroglobulin-thrombin complex, an alternative enzyme with the amidolytic but not the physiological activity of thrombin is staphylocoagulase produced by the bacteria *Staphylococcus aureus*. This enzyme is able to bind to prothrombin present in plasma. The staphylocoagulase-prothrombin complex is able to convert small thrombin substrates without being inhibited by AT. For instance, staphylocoagulase, staphylocoagulase-prothrombin or $\alpha_2$M-thrombin complexes are added to a test sample in an amount usually ranging from 5 to 1000 nanomoles per liter, preferably around 100 nanomoles per liter.

The curves produced by the method of the present invention are characterised by such parameters as lag time, area under the curve, peak height, steepness of ascending slope, time to peak and further all parameters of a curve that resembles the mathematical function $T=a.t^b.\exp{-ct}$ (starting after a lag time). The concentration of thrombin typically starts at zero, rises to a peak height of usually a value between 50 and 500 nanomolar and goes back to zero again. The lag time is usually a value between zero and 20 minutes and is finished as soon as the thrombin concentration is approximately above 10 nanomolar. At this moment also the formation of a clot appears, whereas the peak occurs a few minutes later. The parameters of the thrombin generation curve, also designated as Thrombogram®, a registered trademark of Synapse B.V., described here are composite parameters that are influenced by a large set of concentrations and reaction constants of the interacting clotting factors. They reflect all variations of these variables that influence the function of the haemostatic thrombotic system such as they take place in a clinical, therapeutical or other setting. All antithrombotics and all diseases related to the haemostatic thrombotic system measured thus far have their influence on these parameters. During antithrombotic treatment or haemostatic coagulation disorders of any kind lag times and time to peak values are usually increased, peak height and area under the curve are usually decreased. On the other hand under hypercoaguable states these parameters move into the opposite direction. In this way the Thrombogram truly reflects the clottability of blood and gives an indication for either thrombotic or haemostatic risk.

The present invention further relates to a kit for carrying out the method of the present invention as herein described, as well as to the equipment for routinely carrying out the determination of the inventive method and to supplying a source of test components in bulk quantity for facilitating the operation of automated appliances which can process large amounts of test samples.

In a preferred embodiment the test kit suitably comprises:
1. A thrombin "calibrator" consisting of a known concentration of $\alpha_2$-macroglobulin-thrombin complex, optionally in lyophilized form;
2. A PRP-reagent which is intended for Platelet-Rich-Plasma and contains a trigger to start the clotting reaction, usually thromboplastin or recombinant relipidated Tissue Factor or soluble Tissue Factor optionally in lyophilized form. Alternatively, it may contain a trigger that activates the intrinsic system such as elagic acid or kaolin.
3. A PPP-reagent which is intended for Platelet-poor or Platelet-free plasma that contains phospholipid vesicles in combination with thromboplastin or recombinant relipidated Tissue Factor or soluble Tissue Factor, optionally in lyophilized form. Alternatively, it may contain a trigger that activates the intrinsic system such as elagic acid or kaolin.
4. A reagent which contains compounds from the PPP or PRP reagents plus specific compounds that makes the Thrombogram more sensitive to specific abnormalities in the clotting system. For instance, PPP-reagent without phospholipid would make the Thrombogram sensitive for microparticles that are present in plasma. PPP or PRP reagent to which Thrombomodulin or Activated Protein C (APC) is added would make the Thrombogram more sensitive to all disorders of the natural anticoagulant system known as the protein C system. PPP or PRP reagent to which Activated Protein C (APC) is added would make the Thrombogram sensitive to factor V Leiden or other congenital or acquired forms of so-called APC resistance of factor V and/or factor VIII. PRP- or PPP-reagent without Tissue Factor would make the Thrombogram sensitive to the presence of endogenous Tissue Factor activity present in the sample (see Giesen et al., Proc Natl Acad Sci USA 1999 96(5):2311-5.).
5. A reagent that contains a signal substrate such as Z-Gly-Gly-Arg-AMC and usually also calcium ions.
6. A software program to facilitate the calculation of the corrections which are included in the present method to obtain the concentration of thrombin in time. A suitable software program which is specially designed for carrying out the method of the present invention and designated under the trade mark Thrombinoscope® is obtainable from the applicant Synapse B.V. which can be contacted through its website www.thrombin.com or by email: info@thrombin.com.
7. A manual with instructions how the kit is to be used may also form part of the test kit.

The difference between PPP and PRP reagent resides in the content of phospholipids, this should be low in the case of PRP in order to be able to measure the contribution of platelets in thrombin formation.

The test kit is conveniently used as follows: To 80 microliter of PPP 20 microliter of PPP reagent is added and to another 80 µL sample of the same plasma 20 µL of Thrombin Calibrator is added. Subsequently 20 microliter of a mixture of fluorogenic substrate and calcium is added to both samples and the reaction is followed in a fluorometer.

It will be understood to those skilled in the art that the method and kit of the present invention are not restricted to the use with fluorogenic substrates but can potentially be applied to chromogenic, NMR, chemiluminescence and other similar assay methods. However, currently fluorogenic substrates are the preferred choice, since in contrast to any other available method assessments can be made in the presence of fibrin, and thus the thrombin on the fibrin is also measured. Furthermore, defibrination which is often troublesome can be avoided, resulting in a simpler and more reliable method which can be easily operated in the clinic. In addition, the present method using a fluorogenic substrate now permits assessments of thrombin in the presence of platelets (as is well known in the art, fibrin is needed for the activation of platelets), and therefore antiplatelet drugs can be tested, and platelet-pathologies can be measured, thus enabling a more adequate treatment.

Figure 9:
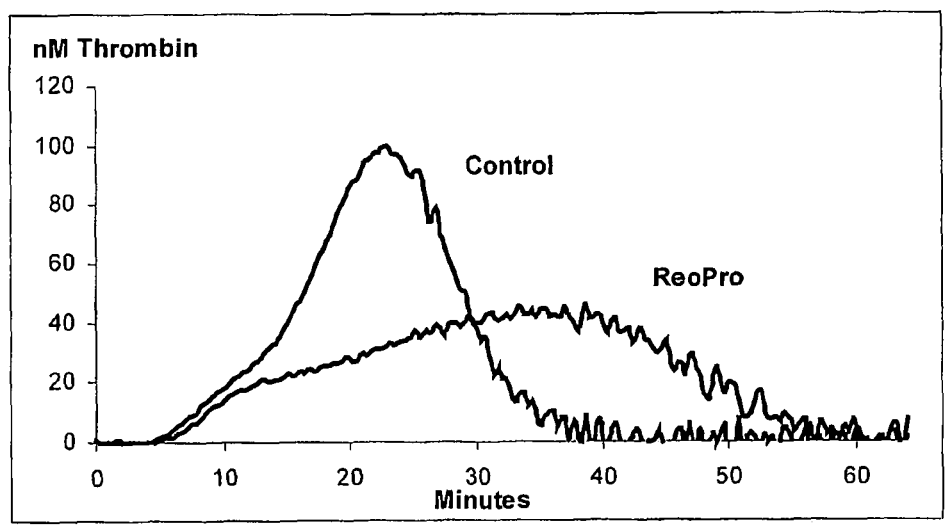
FIG. 9 shows the thrombin generation curves in platelet-rich plasma of a healthy donor and in the same plasma treated with a platelet-activation inhibitor, respectively.

FIG. 9 is an example of an experiment in which platelet-rich plasma of a healthy donor is measured as well as the same plasma treated with a known platelet-activation inhibitor (ReoPro®). The two curves are different in shape, which is obvious from a longer TTP and lower peak height, but the area under the curve of both curves are within 3%, identical. This effect on peak height and TTP in the absence of a clear effect on the ETP is also seen for many mild coagulation factor deficiencies such as von Willebrand disease, deficiencies in factor VII or factor V and in factor VIII or IX deficiencies (haemophiliae). In many instances the Peak height and TTP have proven to be much more sensitive parameters of the thrombin generation curve than the ETP alone.

The method according to the present invention can be suitably used to diagnose hyper- and hypocoaguable states, either congenital, acquired or drug-induced in humans and animals and hence to monitor prophylactic or therapeutic therapy with antithrombotics and in general all drugs that influence the function of the clotting system and all diseased states characterised by malfunction of this system.

The invention will now be further Illustrated by the following examples which are not to be construed as limiting the scope of the invention in any respect.

EXPERIMENTAL

1. Preparation of a Thrombin Calibrator
Isolation of $\alpha_2$-Macroglobulin
Raw $\alpha_2$-macroglobulin ($\alpha_2$M) is prepared according to Barrett, A J., *Alpha 2-macroglobulin, Methods Enzymol* (1981) 80 (Pt C) p. 737-54. The material is isolated from citrated bovine plasma. The procedure is followed until the α$_2$M is precipitated in 12% (w/v) PEG-20,000. The pellet is dissolved in 100 mM NaCl, 20 mM HEPES (pH 7.9) and used to prepare α$_2$M-thrombin complex (α$_2$M-T).

Preparation of α$_2$-Macroglobulin-Thrombin Complex

To the α$_2$M is added 12 μM bovine prothrombin, 6 mM CaCl$_2$, 50 μM phospholipid vesicles (20% brain phosphatidyl serine, 80% egg-yolk phosphatidyl choline), 5 nM bovine factor Xa and 0.78 nM bovine factor Va. This mixture is stirred 30 min. at room temperature and then kept overnight at 4° C. Formed clots are removed and the preparation is divided into suitable amounts for purification by gel filtration (size exclusion chromatography); i.e. in amounts of 40 ml in our case. The preparation now can be frozen at −80° C. until further processing.

40 ml of α$_2$M-T is applied to a Sephacryl column (20 cm$^2$×90 cm) which is equilibrated with 100 mM sodium citrate. 20 mM HEPES (pH 7.4), 0.02% NaN$_3$. The column is run with equilibration buffer with 0.7 m/min for 700 ml and then with 3 ml/min. Fractions with retention volume 774-846 ml contain α$_2$M-T. The material elutes in a sharp peak.

The concentration of α$_2$M-T is measured by its ability to hydrolyze the chromogenic substrate S2238. The ability to hydrolyze a chromogenic substrate is called amidolytic activity. The amidolytic activity of the preparation is adjusted to the same activity of 600 nM human thrombin and then 100 nM bovine antithrombin and 2 U/ml heparin (LEO) are added, The material now is ready for use as a thrombin calibrator. If desired the material can be lyophilized in suitable amounts.

2. Addition of Thrombin or α$_2$M-Thrombin to Plasma

When thrombin is added to plasma, its activity immediately decreases due to the natural inhibitors of thrombin present in plasma. On the other hand, the same activity of α$_2$M-thrombin results in a line that curves due to substrate depletion and inner filter effect only FIG. 1 shows the fluorescent signal measured in the well of a 96-well plate to which thrombin (100 nM) or α$_2$M-thrombin complex is added plus the fluorogenic substrate Z-Gly-Gly-Arg-AMC (0.417 μM, available from BACHEM, catalog # I-1140). It can be seen that in contrast to the α$_2$M-thrombin complex (thick line), the activity of the thrombin-curve (symbols) goes down swiftly. In buffer (20 mM Hepes, 140 mM NaCl, 5 g/l bovine serum albumin (BSA), pH 7.35) these two preparations have an identical activity (thin line and symbols) and it is also observed that the fluorescent yield in buffer is higher than that in plasma. This is due to the color of the plasma that differs considerably from that of buffer. Even donor-to-donor variations in color of plasma can give considerable differences in amount of signal. This stresses the need to always compare the thrombin activity in the plasma of a particular donor to the activity of a known calibrator in plasma of that same donor.

3. Estimation of the Activity of the α$_2$M-Thrombin Complex

Figure 2:
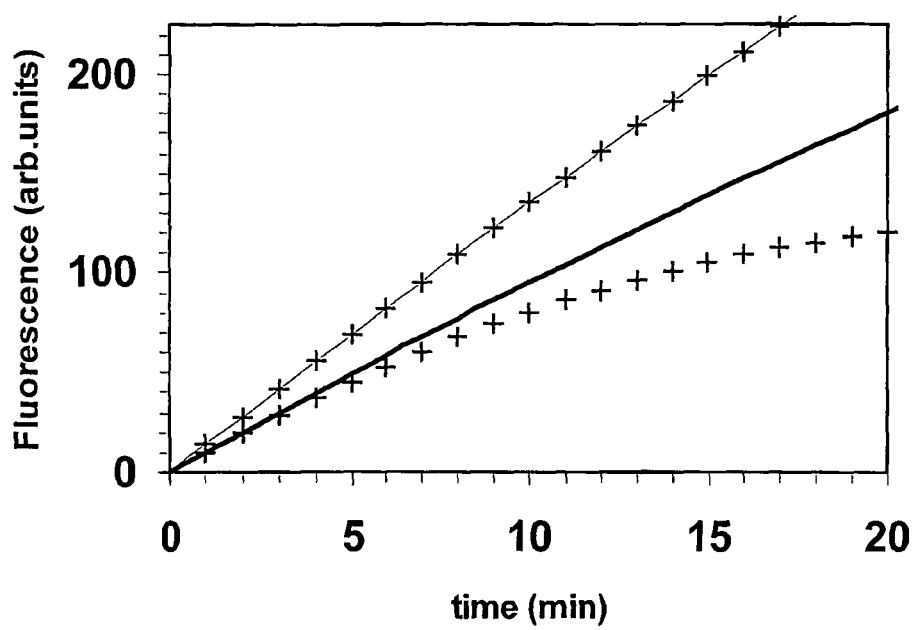
FIG. 2 shows the generation of fluorescent signal upon addition of thrombin (lower symbol line) and $\alpha_2$-macroglobulin-thrombin (thick line) in heated plasma or in buffer (upper symbol line) that contains a fluorogenic substrate.

The amidolytic activity of the calibrator is determined by comparison of its activity with a known amount of human thrombin. The concentration of this human thrombin is determined by active site titration, Thrombin is allowed to interact with a substrate which reacts very rapidly in the first part of the catalytic reaction to release a chromophoric product, e.g. rapid acylation of the enzyme to release a measurable product (e.g. p-nitroaniline), followed by a much slower reaction to complete the turnover reaction. Thus the burst of product is proportional to the number of active sites. From this thrombin the activity in numbers of converted molecules per unit of time per molecule of enzyme is then exactly known. The comparison is carried out under conditions that, as to temperature, pH and substrate concentration, are identical to those in an actual experiment and in a medium in which thrombin is stable within the time limits of the experiment (<30 min). This can be either buffer (see above, see FIG. 2) or heated plasma, i.e. plasma in which the natural inhibitors of thrombin have been inactivated by heating (10 minutes at 70° C.).

4. Automated Fluorogenic Measurement of Thrombin Generation

Firstly, an experiment is described in which thrombin generation in a sample of platelet rich plasma is measured. Solutions used: Human platelet rich plasma, obtained as in Beguin, S., T. Lindhout, and H. C. Hemker. *The effect of trace amounts of tissue factor on thrombin generation in platelet rich plasma, its inhibition by heparin*. Thromb Haemost, 1989. 61(1): p-25-9. Buffer A: 20 mM Hepes 140 mM NaCl, 5 g/l bovine serum albumin (BSA), pH 7.35; Buffer C: 20 mM Hepes, 140 mM NaCl, with BSA 60 mg/mL, pH 7.35 with 0.02% sodium azide as a preservative.

FluCa solution: To 1750 μL of buffer C are added 200 μL of 1 M CaCl$_2$. The mixture is warmed to 37° C. Then 50 μL of 100 mmoles/liter of the substrate solution in DMSO is squirted in and the tube is immediately vortexed to obtain a perfectly clear solution that is 2.5 mM in substrate. 100 mM in CaCl$_2$, 2.5% in DMSO.

Figure 3:
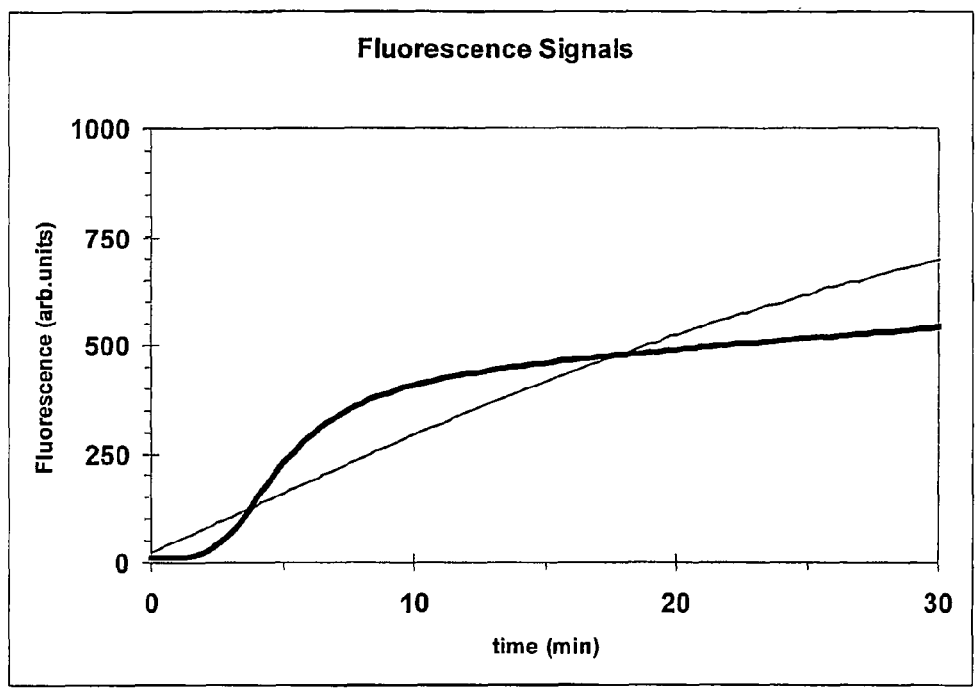
FIG. 3 shows the original fluorescence signals in two identical samples of plasma to which the same concentration of a fluorogenic substrate was added. In one sample a thrombin generation activator was added resulting in thrombin generation. In the other sample a known concentration of $\alpha_2$-macroglobulin-thrombin complex was added which resulted in a stable amidolytic activity.
Thick line: Signal from the sample in which thrombin generation has been activated
Thin line: Signal from the sample to which the α2-macroglobulin-thrombin complex has been added.
Figure 4:
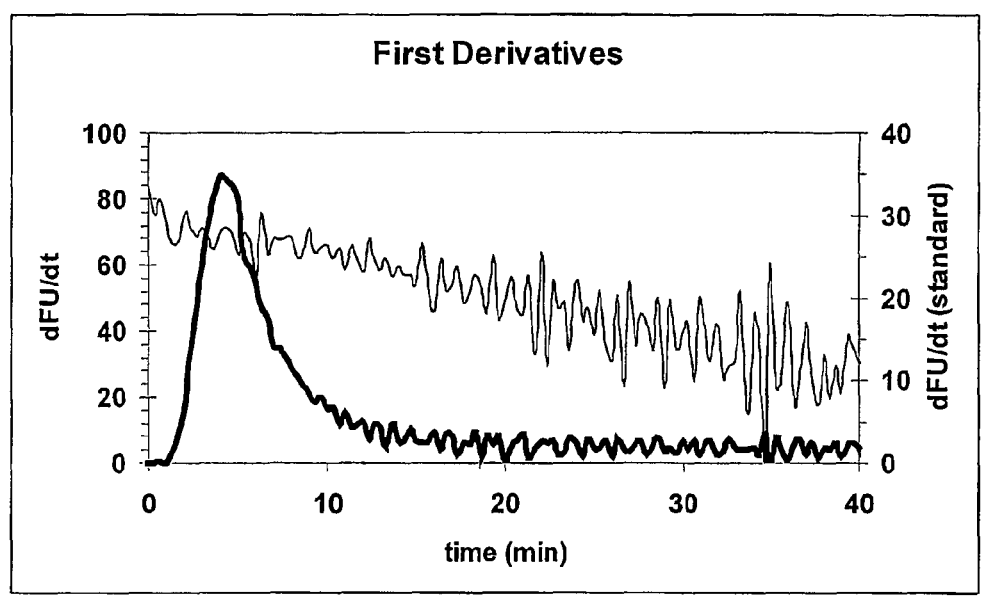
FIG. 4 shows first derivatives of the signals in FIG. 1.
Thick line: dFU/dt from the sample in which thrombin generation took place
Thin line: dFU/dt from the sample to which the known concentration of $\alpha_2$-macroglobulin-thrombin complex has been added.

A microtiter plate fluorometer (Fluoroscan Ascent, Thermolab Systems, Helsinki, Finland) was thermostated at 37° C. In a 96-well round bottom plate 20 μL of prewarmed trigger solution consisting of a 30 picomolar recombinant tissue factor concentration in buffer A was added to one well and 20 μL of prewarmed calibrator consisting of an α$_2$M-thrombin complex concentration of 600 nanomolar to another 80 μL of plasma was added to each of these wells. The dispenser of the fluorometer was filled with FluCa solution and the experiment was started. FIG. 3 shows the fluorescent signals that evolved. The first derivatives of the obtained signal is shown in FIG. 4.

The first derivatives shown in FIG. 3 do not truly represent the thrombin-time curve for three reasons: a) the product-fluorescence relationship is not linear, because the fluorescent molecules also absorb light at the measuring wavelength (inner filter effect), b) the substrate is consumed, and c) α2-macroglobulin-thrombin builds up from the thrombin generating in the experiment and the α2-macroglobulin normally present in any plasma.

The effect of α2M-thrombin building up during the experiment is a common feature of all thrombin generation measurements in which thrombin is estimated by its amidolytic activity on a small signal-substrate, subsampling and continuous methods alike. The way to correct for this effect has been published and is well known to people skilled in the art [Hemker, H. C. and S. Beguin, *Thrombin generation in plasma: its assessment via the endogenous thrombin potential*. Thromb Haemost, 1995. 74(1): p. 134-8].

The disturbing effects a and b are corrected by continuous on line comparison of the first derivative of the signal from the thrombin generated in the sample (O=f(t)) and the first derivative of the signal produced in the other sample by the calibrator (S=f(t)). The latter is in good approximation a straight line fitting the formula S=B−A*t. A and B are continuously calculated during the experiment from the best fitting straight line through S=f(t). The corrected values (R) are obtained via the following formula:

$$R(t)=B*SQRT(((B^2-4*A)*O(t))/(2*A))-(B^2/(2*A))$$

Figure 5:
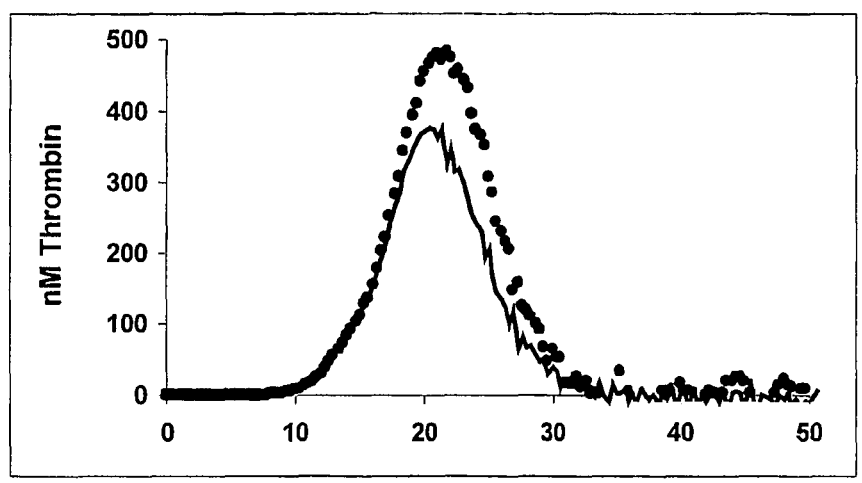
FIG. 5 shows two thrombin generation curves in plasma.
Thick line: thrombin concentration in time that has not been corrected for substrate consumption or inner filter effect and Symbol line: thrombin concentration in time after correction for substrate consumption and inner filter effect. In both cases the concentration of thrombin was determined from the initial velocity of conversion of the fluorogenic substrate by a known activity of α2-macroglubulin-thrombin complex in plasma.

The resulting curve R=f(t) is continuously displayed during the experiment on the screen of a computer that carries out these experiments (FIG. 5A en B).

5. Simultaneous Experiments

Figure 6:
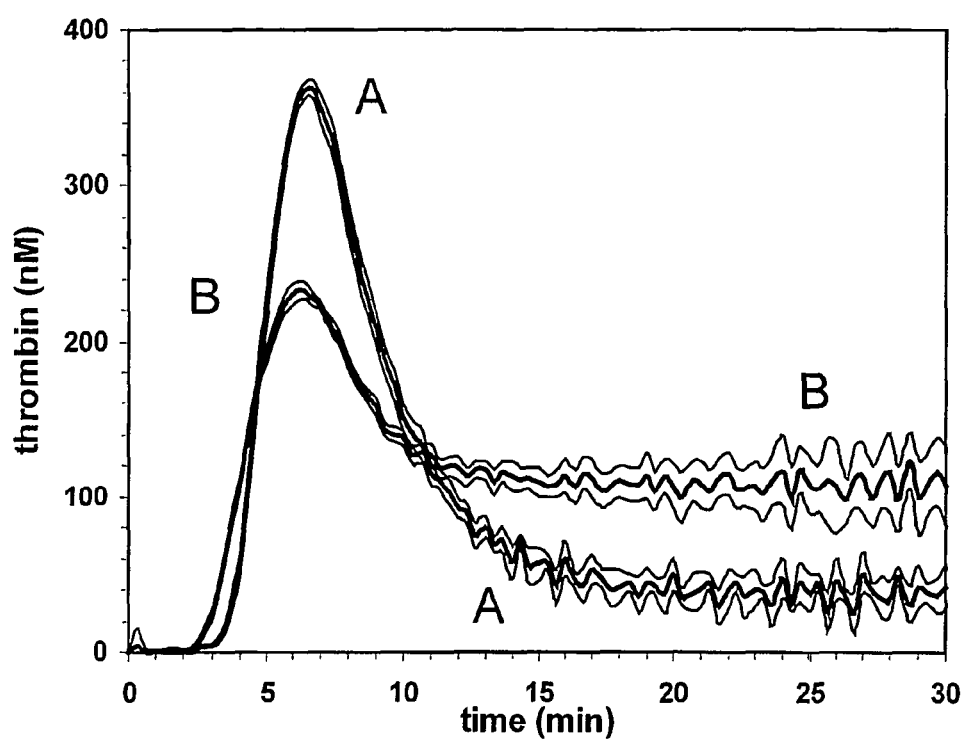
FIG. 6 shows the mean and the confidence limits of the signals from 24 simultaneous determinations of thrombin generation. Curve A depicts normal plasma and Curve B depicts normal plasma from which fibrinogen is removed.

The experiment described sub 4 requires two wells in a 96 well plate. It can as well be performed simultaneously in any number of the available wells, for either duplicate or different experiments. The only requirement being that always an experiment in a given plasma is accompanied by the registration of the signal from the calibrator in another sample of that same plasma. FIG. 6 shows the mean and the confidence limits of the signals from 24 simultaneous experiments. It is seen that the amount of thrombin generated in the presence of fibrin(ogen) is higher, which indicates that the method does pick up the activity of clot bound thrombin.

Figure 7:
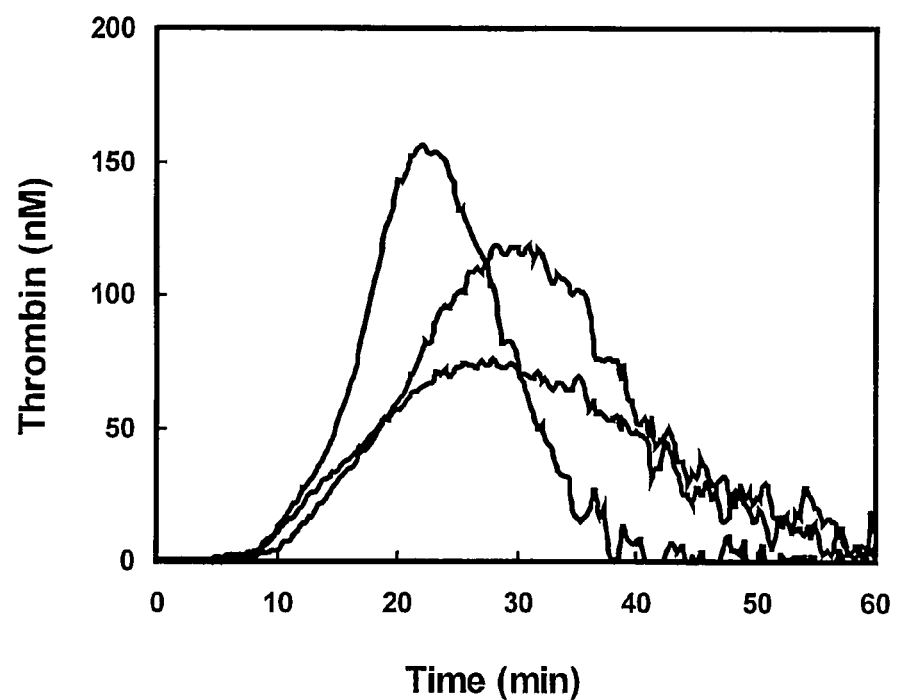
FIG. 7 shows the thrombin curves from three individuals measured simultaneously in quadruple each.
Figure 8:
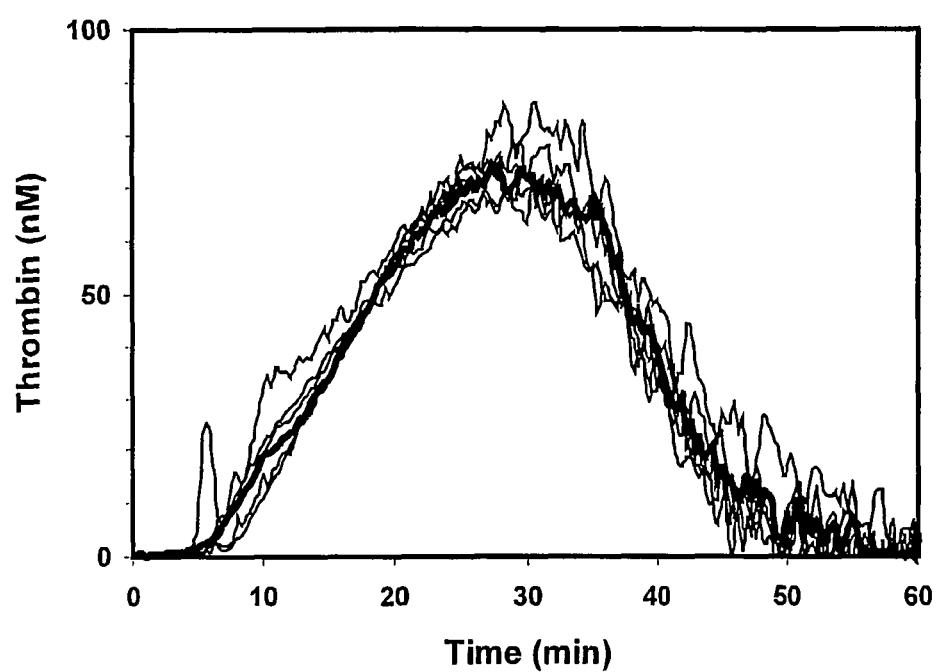
FIG. 8 shows the curves from the PRP of one individual, measured in quadruple on six different days.

FIG. 7 shows the curves from three different individuals simultaneously measured in quadruple each. FIG. 8 shows the curves from the PRP of one individual, measured in quadruple on six different days.

The present invention offers a convenient test method to determine in real time the course of proteolytic activity in a biological sample, in particular thrombin activity in blood or plasma, which is provided as a continuous signal thereby giving more valuable and accurate information regarding such parameters as lag time and peak height, as compared with methods belonging to the state of the art such as the ETP-method according to which only end-point determinations of the amount of product can be made.

The present disclosure is to be considered as in all respects illustrative and not restrictive, the scope of the invention being indicated by the appended claims, and all changes which come within the meaning and range of equivalency are intended to be embraced therein.

The invention claimed is:

1. A method for determining in real time the course of thrombin activity in a biological sample as it appears in and disappears from the sample comprising the following steps:
    a) adding a protease activator to a first portion of said sample to generate thrombin activity to produce an activated sample;
    b) adding a signal substrate to the activated sample of step a), such that a detectable signal related to the amount of conversion product is formed upon reaction by the generated thrombin activity;
    c) adding a known stable proteolytic activity selected from the group consisting of α2-macroglobulin-thrombin complex and staphylocoagulase-prothrombin complex that acts on the same signal substrate as defined in step b) to a second parallel portion of said sample to produce a combined second portion, wherein said proteolytic activity is otherwise inert and said proteolytic activity is not triggered;
    d) adding the same signal substrate as defined in to step b) to the combined second portion of said sample of step c), said signal substrate causing a detectable signal upon reaction by the means with known stable proteolytic activity;
    e) determining the time course of signal development in reaction of step b) and step d) to provide a signal curve from each reaction; and
    f) comparing said curves to derive the course of thrombin activity in time in the sample.

2. A method according to claim 1, wherein the sample is blood or plasma.

3. A method according to claim 1, wherein the biological sample is selected from the group consisting of blood, plasma, inclusive platelet-rich, platelet-poor or platelet-free plasma, saliva, serum, urine, cerebrospinal fluid, sperm, and faeces.

4. A method according to claim 1, wherein the signal substrate is selected from the group consisting of compounds comprising a leaving group, said leaving group giving a detectable conversion product upon reaction by the proteolytic enzyme formed.

5. A method according to claim 4, wherein the signal substrate is Z-Gly-Gly-Arg-AMC.

6. A method according to claim 4, wherein the detectable conversion product is determined by spectroscopy, in particular fluorescence, optical density, and NMR.

7. A method according to claim 4, wherein the leaving group is a fluorescent group, a chromophoric group or a group releasing hydrogen ions.

8. A method according to claim 4, wherein the detectable conversion product is p-nitroanilide or 7-amino-4-methylcoumarin.

9. A method according to claim 1, wherein the protease activator is selected from the group consisting of calcium ions, phospholipids, Tissue Factor, soluble Tissue factor, thromboplastin, kaolin, and elagic acid.

10. A method according to claim 1, wherein said biological sample further comprises a pharmaceutical agent to be tested for its influence on the haemostatic-thrombotic system.

11. A method according to claim 10, wherein the pharmaceutical agent is an antithrombotic agent comprising an antiplatelet agent or an anticoagulant agent.

12. A method according to claim 11, wherein the antithrombotic agent is selected from the group consisting of heparin, dermatan sulphate, direct thrombin-inhibitors selected from hirudin, argatroban or melagatran, and the factor Xa inhibitor tick anticoagulant protein.

13. A method according to claim 1, wherein the known stable proteolytic activity is staphylocoagulase-prothrombin complex.

* * * * *